United States Patent [19]
Rodgers et al.

[11] Patent Number: 5,534,261
[45] Date of Patent: Jul. 9, 1996

[54] RETINOID-BASED COMPOSITIONS AND METHOD FOR PREVENTING ADHESION FORMATION USING THE SAME

[75] Inventors: Kathleen E. Rodgers, Long Beach; Gere S. Dizerega, Pasadena, both of Calif.

[73] Assignee: University of Southern California, Los Angeles, Calif.

[21] Appl. No.: 373,399

[22] Filed: Jan. 17, 1995

[51] Int. Cl.$^6$ ................................... A61K 9/127
[52] U.S. Cl. ..................... 424/450; 424/422; 424/443; 424/484; 424/489; 514/559
[58] Field of Search ................... 514/559; 424/450, 424/422, 443, 484, 489

[56] References Cited

U.S. PATENT DOCUMENTS

| | | | |
|---|---|---|---|
| 4,171,318 | 10/1979 | Chan et al. | 260/404 |
| 4,200,647 | 4/1980 | Bollag et al. | 424/305 |
| 4,231,944 | 11/1980 | Chan et al. | 260/347.4 |
| 4,326,055 | 4/1982 | Loeliger | 542/429 |
| 4,395,575 | 7/1983 | Chan et al. | 568/442 |
| 4,396,553 | 8/1983 | Klaus | 260/456 |
| 4,544,770 | 10/1985 | Broger | 568/9 |
| 4,556,518 | 12/1985 | Lucci | 260/413 |
| 4,565,863 | 1/1986 | Bollag et al. | 536/18.2 |
| 4,863,969 | 9/1989 | Bollag | 514/765 |
| 4,870,219 | 9/1989 | Klaus et al. | 570/189 |
| 4,883,613 | 11/1989 | Aig et al. | 260/408 |
| 4,894,480 | 1/1990 | Aig et al. | 568/11 |
| 4,900,478 | 2/1990 | Gross | 260/408 |
| 4,935,560 | 6/1990 | Klaus et al. | 570/189 |
| 4,937,254 | 6/1990 | Sheffield et al. | 514/420 |
| 4,990,703 | 2/1991 | Klaus et al. | 570/189 |
| 5,001,276 | 3/1991 | Klaus et al. | 568/609 |
| 5,030,764 | 7/1991 | Klaus et al. | 568/327 |
| 5,030,765 | 7/1991 | Klaus et al. | 568/327 |
| 5,055,622 | 10/1991 | Klaus et al. | 568/609 |
| 5,075,333 | 12/1991 | Bryce et al. | 514/481 |
| 5,158,773 | 10/1992 | Gross | 424/401 |
| 5,242,909 | 9/1995 | Teelmann | 514/110 |
| 5,252,604 | 10/1993 | Nagy et al. | 514/559 |
| 5,360,789 | 11/1994 | Nakao | 514/12 |

FOREIGN PATENT DOCUMENTS

| | | |
|---|---|---|
| 0100839B1 | 2/1984 | European Pat. Off. |
| 0111325B1 | 6/1984 | European Pat. Off. |
| 0263493A2 | 4/1988 | European Pat. Off. |
| 0263492A1 | 4/1988 | European Pat. Off. |
| 0274104A2 | 7/1988 | European Pat. Off. |
| 0303915B1 | 2/1989 | European Pat. Off. |
| 0439042A1 | 7/1991 | European Pat. Off. |
| 0552624A1 | 7/1993 | European Pat. Off. |
| 0552612A2 | 7/1993 | European Pat. Off. |
| 0568898A1 | 11/1993 | European Pat. Off. |
| 2190378 | 11/1987 | United Kingdom |
| 9007571 | 7/1990 | WIPO |

OTHER PUBLICATIONS

Weiyong, CA 122, 96387 1994.

Varani J. Invest. Dermatol. 93 #4, p. 449 (1989).

Abe et al. (1990), "The Effect of Intraperitoneal Administration of Sodium Tolmetin-Hyaluronic Acid on the Post-surgical Cell Infiltration In Vivo," *J. Surg. Res.*, vol. 49, pp. 322–327.

Batova et al. (1992), "Retinoic Acid Induces Secretion of Latent Transforming Growth Factor $\beta_1$ and $\beta_2$ in Normal and Human Papillomavirus Type 16–immortalized Human Keratinocytes," *Cell Growth & Differentiation*, vol. 3, pp. 763–772.

Boehm et al. (1994), "Synthesis of High Specific Activity [$^3$H]–9–cis–Retinoic Acid and Its Application for Identifying Retinoids with Unusual Binding Properties," *J. Med. Chem.*, vol. 37, pp. 408–414.

Chatelut et al. (1993), "A Slow–Release Methotrexate Formulation for Intrathecal Chemotherapy," *Cancer Chemother. Pharmacol.*, vol. 32, pp. 179–182.

Conese et al. (1991), "Inhibitory Effect of Retinoids on the Generation of Procoagulant Activity by Blood Nononuclear Phacocytes," *Thrombosis and Haemostasis*, vol. 66, pp. 662–665.

Diamond et al. (1991), "Synergistic Effects of INTERCED (TC7) and Heparin in Reducing Adhesion Formation in the Rabbit Uterine Horn Model," *Fertility and Sterility*, vol. 55, pp. 389–394.

Diamond et al. (1991), "Adhesion Reformation: Reduction by the Use of Interceed (TCU) Plus Heparin," *J. Gynecologic Surgery*, vol. 7, pp. 1–6.

diZerega and Rodgers (1992), "Prevention of Postoperative Adhesions", in *The Peritoneum*, diZerega and Rodgers, eds., Springer–Verlag, New York, pp. 307–369.

Doepner et al. (1992), "Effects of Novel Retinoids on Growth and Differentiation of a Rhabdomyosarcoma Cell Line," *Arzneim.–Forsch/Drug. Res.*, vol. 42, pp. 1036–1040.

Elkins, Thomas (1990), "Can a Pro–Coagulant Substance Prevent Adhesions,?" in *Treatment of Post–SurgicalAdhesions*, diZerega et al., eds., Wiley–Liss, New York, pp. 103–112.

Fumarulo et al. (1991), "Retinoids Inhibit the Respiratory Burst and Degranulation of Stimulated Human Polymorphonuclear Leukocytes," *Agents and Actions*, vol. 34, pp. 339–344.

(List continued on next page.)

*Primary Examiner*—Gollamudi S. Kishore
*Attorney, Agent, or Firm*—Banner & Allegretti, Ltd.

[57] ABSTRACT

Compositions and methods for prevention of adhesion formation, whereby an effective amount of at least one retinoid, e.g., all trans retinoic acid, is administered for a period of time sufficient to permit tissue repair. The retinoid is preferably administered in conjunction with a delivery vehicle (e.g., microcapsules, microspheres, biodegradable polymer films, lipid-based delivery systems such as liposomes and lipid foams, viscous instillates and absorbable mechanical barriers) useful for maintaining local concentrations of the compound at the injury site at an effective level.

20 Claims, No Drawings

OTHER PUBLICATIONS

Giordano et al. (1993), "Sustained Delivery of Retinoic Acid from Microspheres of Biodegradable Polymer in PVR," *Investigative Ophthalmology & Visual Science*, vol. 34, pp. 2743–2751.

Glasser et al. (1994), "Functional Characteristics of In Vivo Induced Neutrophils After Differentiation Therapy of Acute Promyelocuytic Leukemia with All–Trans–Retinoic Acid," *Cancer*, vol. 73, pp. 1206–1212.

Goettsch et al. (1992), "Adjuvant Activity of All–Trans–Retinoic Acid in C57B1/6 Mice," *J. Immunopharmac.*, vol. 14, pp. 143–150.

Hamasaki et al. (1994), "Specific Induction of LTC4 Synthase by Retinoic Acid in Rat Basophilic Leukemia–1 Cells," *Int. Arch. Allergy Immunol.*, vol. 103, pp. 260–265.

Hershlag et al. (1991), "The Effect of Interleukin–1 on Adhesion Formation in the Rat," *Am. J. Obstet. Gynecol.*, vol. 165, pp. 771–774.

Hockel et al. (1987), "Prevention of Peritoneal Adhesions in the Rat with Sustained Intraperitoneal Dexamethasone Delivered by a Novel Therapeutic System," *Annales Chirurgiae et Gynaecologiae*, vol. 76, pp. 306–313.

Horie et al. (1992), "Retinoic Acid Stimulates Expression of Thrombomoduli, a Cell Surface Anticoagulant Glycoprotein, on Human Endothelial Cells," *Biochem. J.*, vol. 281, pp. 149–154.

Immonen et al. (1993), "Retinoids Increase Urokinase–Type Plasminogen Activator Production by Human Retinal Pigment Epithelial Cells in Culture," *Invest. Ophthalmol.*, vol. 34, pp. 2062–2067.

Ishii et al. (1992), "Retinoic Acid Counteracts Both the Downregulation of Thrombomodulin and the Induction of Tissue Factor in Cultured Human Endothelial Cells Exposed to Tumor Necrosis Factor," *Blood*, vol. 80, pp. 2556–2562.

Johnson and Johnson (1989), "Prevention of Postsurgical Adhesions by INTERCEED (TC7), an Absorbable Adhesion Barrier: A Prospective Randomized Multicenter Clinical Study," *Fertility and Sterility*, vol. 51, pp. 933–938.

Kim et al. (1992), "Effect of Topical Retinoic Acids on the Levels of Collagen mRNA During the Repair of UVB–Induced Dermal Damage in the Hairless Mouse and the Possible Role of TGF–$\beta$ as a Mediator," *J. Investigative Dermatology*, vol. 98, pp. 359–363.

Kim et al. (1993), "Extended–Release Formulation of Morphine for Subcutaneous Administration," *Cancer Chemother. Pharmacol.*, vol. 33, pp. 187–190.

Kistler et al. (1990), "Teratogenicity of Arotinoids (Retinoids) In Vivo and In Vitro," *Arch. Toxicol.*, vol. 64, pp. 616–622.

Lewis, Danny (1990), "Controlled Release of Bioactive Agents from Lactide–Glycolide Polymers," in Biodegradable Polymers as Drug Delivery Systems, Jason & Langer, eds., pp. 1–41.

McBride et al. (1989), "Effect of Interleukin 1, Inflammation, and Surgery on the Incidence of Adhesion Formulation and Death After Abdominal Irradiation in Mice," *Cancer Research*, vol. 49, pp. 169–173.

Medh et al. (1992), "Stimulation of Tissue Plasminogen Activator Production by Retinoic Acid: Synergistic Effect on Protein Kinase C–Mediated Activation," *Blood*, vol. 80, pp. 981–987.

Mehta et al. (1994), "Inhibition by All–Trans–Retinoic Acid of Tumor Necrosis Factor and Nitric Oxide Production by Peritoneal Macrophages," *J. Leukocyte Biology*, vol. 55, pp. 336–342.

Nair et al. (1991), "BMY 30047: A Novel Topically Active Retinoid with Low Local and Systemic Toxicity," *J. Pharmacology & Experimental Therapeutics*, vol. 256, pp. 365–370.

Nishimura et al. (1984), "Ibuprofen in the Prevention of Experimentally Induced Postoperative Adhesions," *Am. J. Med.*, vol. 77, pp. 102–106.

Oikawa et al. (1993), "Three Novel Synthetic Retinoids, Re 80, Am 580 and Am 80, All Exhibit Anti–Angiogenic Activity In Vivo," *European J. Pharmacology*, vol. 249, pp. 113–116.

Repa et al. (1993), "All–trans–retinol is a Ligand for the Retinoic Acid Receptors," *Proc. Natl. Acad. Sci. USA*, vol. 90, pp. 7293–7297.

Rodgers et al. (1988), "Effects of Tolmetin Sodium Dihydrate on Normal and Postsurgical Peritoneal Cell Function," *Int. J. Immunopharmac.*, vol. 10, pp. 111–120.

Rodgers et al. (1990), "Intraperitoneal Tolmetin Prevents Postsurgical Adhesion Formation in Rabbits," *Int. J. Fertil.*, vol. 35, pp. 40–45.

Rodgers, K. (1990), "Nonsteroidal Anti–inflammatory Drugs (NSAIDs) in the Treatment of Postsurgical Adhesion," in Treatment of Post Surgical Adhesions, Wiley–Liss, Inc., pp. 119–129.

Schuster et al. (1993), "Retinoic Acid Potentiates Phorbol Ester–Mediated Induction of Urokinase and Plasminogen Activatory Inhibitor Type 2 in Human Myeloid Leukemic Cell Lines," *Endocrinology*, vol. 133, pp. 1724–1730.

Takino et al. (1994), "Long Circulating Emulsion Carrier System for Highly Lipophilic Drugs," *Biol. Pharm. Bull.*, vol. 17, pp. 121–125.

Tokura et al. (1992), "Retinoid Augmentation of Bioactive Interleukin–1 Production by Murine Keratinocyutes," *British J. Dermatology*, vol. 126, pp. 485–489.

Torma et al. (1993), "Biologic Activities of Retinoic Acid and 3,4–Didehydroretinoic Acid in Human Keratinocytes Are Similar and Correlate with Receptor Affinities and Transactivation Properties," *J. Invest. Dermatol.*, vol. 102, pp. 49–54.

Tramposch et al. (1992), "The Pharmacology of a Novel Topical Retinoid, BMY 30123: Comparison with Tretinoin," *J. Pharm. Pharmacol.*, vol. 44, pp. 379–386.

Turton et al. (1992), "Comparative Teratogenicity of Nine Retinoids in the Rat," *Int. J. Exp. Path.*, vol. 73, pp. 551–563.

Van Bennekum et al. (1993), "Modulation of Tissue–type Plasminogen Activator by Retinoids in Rat Plasma and Tissues," *Am. J. Physiol.*, vol. 33, pp. R931–R937.

van Giezen et al. (1993), "Retinoic Acid Enhances Fibrinolytic Activity In–Vivo by Enhancing Tissue Type Plasminogen Activator (t–PA) Activity and Inhibits Venous Thrombosis," *Thrombosis and Haemostasis*, vol. 69, pp. 381–386.

Williams et al. (1992), "Effect of Transforming Growth Factor $\beta$ on Postoperative Adhesion Formation and Intact Peritoneum," *J. Surgical Research*, vol. 52, pp. 65–70.

Wilhite et al., (1992), "Structure–Affinity Relationships of Retinoids with Embryonic Cellular Retinoic Acid–Binding Protein," *Toxicol. Appl. Pharmacol.*, vol. 112, pp. 144–153.

Yang et al. (1993), "Induction of Interleukin-8 Expression in Neuroblastoma Cells by Retinoic Acid: Implication of Leukocyte Chemotaxis and Activation," *Pediatric Research*, vol. 34, pp. 720–724.

Zitnik et al. (1992), "Retinoic Acid Inhibition of IL-1-Induced IL-6-Production by Human Lung Fibroblasts," *J. Immunol.*, vol. 152, pp. 1419–1427.

RETINOID-BASED COMPOSITIONS AND METHOD FOR PREVENTING ADHESION FORMATION USING THE SAME

FIELD OF THE INVENTION

The present invention relates to retinoids and their use thereof in a method for preventing post-operative adhesion formation between organ surfaces.

BACKGROUND OF THE INVENTION

Adhesion formation, in particular following peritoneal surgery, is a major source of postoperative morbidity and mortality. Appendectomy and gynecologic surgery are the most frequent surgical procedures implicated in clinically significant adhesion formation. The most serious complication of intraperitoneal adhesions is intestinal obstruction; in addition, adhesions are associated with chronic or recurrent pelvic pain and infertility in females.

The pathogenesis of adhesion formation is complex and not entirely understood. The first step is believed to involve excess fibrin deposition to form a scaffold. Organization of the fibrin scaffold by cellular elements, including fibroblasts and mesothelial cells, then follows.

Various approaches for the prevention of adhesion formation have been actively explored [diZerega, G. S. & Rodgers, K. E., "Prevention of Postoperative Adhesions," in "The Peritoneum," diZerega, G. S. & Rodgers, K. E., eds., Springer-Verlag, N.Y., pp. 307–369 (1992)]. In general, the treatments fall into three categories: prevention of fibrin deposition in the peritoneal exudate, reduction of local tissue inflammation; and removal of fibrin deposits.

Therapeutic attempts to prevent fibrin deposition include peritoneal lavages to dilute or wash away fibrinous exudate, surgical techniques to minimize tissue ischemia and introduction of barriers to limit apposition of healing serosal surfaces. Although the use of agents affecting coagulation of the fibrinous fluid has also bee proposed, results obtained to date suggest that the use of procoagulants in areas of substantial bleeding may actually promote adhesion formation [Elkins, T. E. "Can a Pro-Coagulant Substance Prevent Adhesions?" in "Treatment of Post-Surgical Adhesions," diZerega, G. S. et al., eds., Wiley-Liss, N.Y., pp. 103–112 (1990)].

Physical barriers have been used in attempts to prevent adhesion formation by limiting tissue apposition during the critical period of peritoneal healing, thereby minimizing the development of fibrin matrix between tissue surfaces. Barrier agents which have been employed include both mechanical barriers and viscous solutions. Mixed results have been obtained using a barrier comprising a thin sheet of expanded poly-tetrafluoroethylene; in any event, such a membrane is less than ideal, as it must be sutured into place and is nonabsorbable. While an absorbable barrier (for example, a barrier made of oxidized regenerated cellulose) would be preferable, not all studies have demonstrated the efficacy of such barriers in preventing adhesions. Liquid barriers have also been considered for use in preventing adhesions; for example, chondroitin sulfate and carboxymethyl cellulose have both shown some promise in animal models. In addition, solution of dextran 70 (molecular weight =70,000) has been the subject of a number of clinical studies. Not all clinical evaluations of 32% dextran 70 have found a therapeutic effect, however, and the clinical use of the solution is also associated with clinically important side effects.

Anti-inflammatory drugs have been evaluated for their effects on postoperative adhesion formation, as they may limit the release of fibrinous exudate in response to inflammation at the surgical site. Two general classes of these drugs were tested: cortico-steroids and nonsteroidal anti-inflammatory drugs. The results of corticosteroid use in animal studies have generally not been encouraging, and clinical use of corticosteroids is limited by their other pharmacologic properties. While experimental evaluations of nonsteroidal anti-inflammatory drugs in postoperative adhesion formation show promise [Rodgers, K. E., "Nonsteroidal anti-inflammatory drugs (NSAIDs) in the treatment of Postsurgical adhesion," in "Treatment of Post-Surgical Adhesions," diZerega, G. S. et al., eds., Wiley-Liss, N.Y., pp. 119–129 (1990)], clinical evaluations of these drugs for adhesion prevention is needed.

The third approach explored to date involves the removal of fibrin deposits. Although proteolytic enzymes (e.g., pepsin, trypsin and papain) should theoretically augment the local fibrinolytic system and limit adhesion formation, these enzymes are rapidly neutralized by peritoneal exudates rendering them virtually useless for adhesion prophylaxis. While various fibrinolytics (for example, fibrinolysin, streptokinase and urokinase) have been advocated, a potential complication to the clinical use of these enzymes in postoperative therapy is excessive bleeding resulting from their administration. Topical application of a recombinant tissue plasminogen activator (rt-PA) has been shown to reduce adhesion formation in a variety of animal models; further research is necessary to develop suitable delivery systems to provide this drug to the surgical site and identify the postoperative time when adhesion prevention is feasible.

To date, no single therapeutic approach has proven universally effective in preventing formation of postoperative intraperitoneal adhesions. Therefore, there is a need for compositions and methods which may be used safely and effectively to prevent adhesion formation in a variety of different contexts.

OBJECTS OF THE INVENTION

It is an object of the present invention to provide retinoid-based compositions for use in preventing or minimizing adhesion formation.

It is another object of the invention to provide methods for the minimization or prevention of post-surgical adhesion formation employing retinoids.

These and other objects of the invention will be apparent in light of the detailed description below.

SUMMARY OF THE INVENTION

The present invention relates to retinoid-based compositions and their use in a method for the minimization or prevention of adhesion formation comprising administering to a subject an effective amount of a at least one retinoid, e.g., retinoic acid. The retinoid is preferably administered in conjunction with a drug delivery system which maintains an effective concentration of the compound at a site of potential adhesion formation during the perioperative interval.

Pursuant to another aspect of the present invention, adhesion formation is minimized or prevented by administration of at least one retinoid at a site of potential adhesion formation for a period of time sufficient to permit substantial tissue repair (e.g., re-epithelialization or mesothelial repair) at the site.

DETAILED DESCRIPTION OF THE INVENTION

All literature references, patents and patent applications cited in this application are incorporated herein in their entirety.

The present invention is based on the discovery that retinoids, particularly all-trans retinoic acid, can be effectively used to prevent or reduce formation of adhesions between organ surfaces following surgical procedures. Retinoids are a group of natural and synthetic vitamin A analogues whose principal effects on target cells are growth inhibition and induction of differentiation. Retinoids have also been shown to exert immunomodulatory and antiinflammatory functions, however the mechanism of these functions are not well understood. K. Mehta et al. (1994) "Inhibition by all-trans-retinoic acid of tumor necrosis factor and nitric oxide production by peritoneal macrophages," *J. Leuko. Biol.*, Vol. 44, pp. 336–342. It is generally believed, however, that nucleosolic binding proteins, such as nuclear retinoic acid (RA and RX) receptors, are involved in retinoid action. Willhite et al. (1992) "Structure-Affinity Relationships of retinoids with Embryonic Cellular retinoic acid-binding protein," *Toxicol. Appl. Pharmacol.*, Vol. 1123, pp. 144–153; EP 0 552 612 A2, published Jul. 28, 1993.

The inventive composition and method are useful in minimizing or preventing adhesion formation between organ surfaces (not cell-to-cell adhesion) in body cavities, the most common cause of which is prior surgery. Retinoids have been found to be especially effective in preventing the formation of adhesion formation in the peritoneum following surgery. In addition, the present invention finds utility in other contexts, e.g., for cardiovascular, orthopedic, thoracic, ophthalmic, CNS and other uses, where prevention of the formation of adhesions is a significant concern. For example, prevention of adhesion formation or drug loculation during the intraperitoneal administration of chemotherapeutic agent is contemplated as within the scope of the present invention. For the purposes of the following discussion, attention is directed primarily to description of compositions and methods useful in inhibiting peritoneal adhesion formation.

The composition of the invention comprises at least one retinoid such as retinoic acid and derivatives and analogs thereof. The preferred retinoid for use in the invention is all-trans-retinoic acid ((E)-3,7-dimethyl-9-(2,6,6-trimethyl-1-cyclo-hexen-1-yl)-2,4,6,8-nonatetraenoic acid)). Retinoic acid derivatives and analogs thereof which are suitable for topical application are also contemplated for use in practicing the invention.

Suitable, but non-limiting, retinoids for use in the invention include the following literature reported compounds: G. Doepner et al. ((1992) "Effects of novel retinoids on growth and differentiation of a rhabdomyosarcoma cell line," *Arzneim.-Forsch/Drug Res.*, Vol. 42, pp. 1036–1040) disclosed retinoic acid derivatives such as all-trans-retinoic acid-β-D-galactopyranosylester; methyl-(1-O-retinoyl-β-D-glucopyranoside)uronate; all-trans retinyl-β-D-glucuronide; methyl-(1-O-retinyl-2,3,4-tri-O-acetyl-β-D-glucopyranoside)uronate;methyl-(1-O-retinyl-β-D-glucopyranoside)uronate; all-trans-retinoic acid-2,3,4,6-tetra-O-acetyl-β-D-galactopyranosylester; and all-transretinoic acid-2,3,4,6-tetra-O-acetyl-β-D-glucopyranosylester.

A. Kistler et al. ((1990) "Teratogenicity or arotinoids (retinoids) in vivo and in vitro," *Arch. Toxicol.*, Vol. 64, pp. 616–622) disclosed retinoic acid derivatives and analogs such as 13–7410; 19–4788; 40–3387; 18–8093; 40–3267; 40–3229; 40–3695; 19–5867; 41–3205; 18–6622; 19–8401; 15–1549; 19–4787.

X. Nair et al. ((1991) "BMY 30047: a novel topically active retinoid with low local and systemic toxicity," *J. Pharm. and Exp. Therap.*, Vol. 256, pp. 365–370) disclosed retinoic acid derivative BMY 30047 (11-cis, 13-cis-12-hydroxymethylretinoic acid δ-lactone).

T. Oikawa et al. ((1993) "Three novel synthetic retinoids, Re 80, Am 580 and Am 80, all exhibit anti-angiogenic activity in vivo," *Eur. J. Pharm.*, Vol. 249, pp. 113–116) disclosed retinoic acid analogs such as Ch 55 ((E)-4-[3-(3, 5-di-tert-butylphenyl)-3-oxo-1-propenyl]benzoic acid); Re 80 (4-[1-hydroxy-3-oxo-3-(5,6,7,8-tetrahydro-3-hydroxy-5, 5,8,8-tetramethyl-2-naphthalenyl)- 1-propenyl]benzoic acid; Am 580 (4-[(5,6,7,8-tetrahydro- 5,5,8,8-tetramethyl-2-naphthalenyl)carboxamido]benzoic acid); Am 80 (4-[(5,6,7, 8-tetrahydro-5,5,8,8,-tetra-methyl- 2-naphthalenyl)carbamoyl]benzoic acid).

K. M. Tramposch et al. ((1992) "The pharmacology of a novel topical retinoid, BMY 30123: comparison with Tretinoin," *J. Pharm. Pharmacol.*, Vol. 44, pp. 379–386) disclosed retinoic acid derivative BMY 30123 (4-acetamidophenyl retinoate).

H. Törmä et al. ((1994) "Biologic activities of retinoic acid and 3,4-dehydroretinoic acid in human keratinocytes are similar and correlate with receptor affinities and transactivation properties," *J. Invest. Dermatology*, Vol. 102, pp. 49–54) disclosed retinoic acid derivatives and analogs 3,4-didehydroretinoic acid and CD367.

J. A. Turton et al. ((1992) "Comparative teratogenicity of nine retinoids in the rat," *Int. J. Exp. Path.*, Vol. 73, pp. 551–563) disclosed Tretinoin (all-trans-retinoic acid); Isotretinoin (13-cis-retinoic acid); Etretinate; Etretin (Acitretin); N-ethylretinamide; 13-cis-N-ethylretinamide; Fenretinide (N-(4-hydroxyphenyl) retinamide); N-(1H-tetrazol-5-yl)retinamide; and N-butylretinamide.

Willhite et al. (1992), *Tox. and Applied Pharm.*, Vol. 112, pp. 144–153 disclosed retinoic acid derivatives and analogs such as SRI 2712-24 ((E)-9-(2-ethyl-6,6-dimethyl-1-cyclohexen- 1-yl)-3,7-dimethyl-2,4,6,8-nonatetraenoicacid; all-trans-retinal ((E)-3,7-dimethyl-9-(2,6,6-trimethyl-1-cyclohexen- 1-yl)-2,4,6,8-nonatetraenal)); all-trans-retinol ((E)-3, 7-dimethyl-9-(2,6,6-trimethyl-1-cyclo-hexen-1-yl)-2,4,6,8-nonatetraenol); 13-cis-4-oxo-retinoic acid (Ro 22-6595; ((2Z,4E,6E,8E)-3,7-dimethyl-9-(2,6,6trimethyl- 3-oxo-1-cyclo-hexen-1-yl)-2,4,6,8-nonatetraenoic acid); N-(2-hydroxy-ethyl) 13-cis-retinamide ((N-1-(2-hydroxyethyl) (2Z, 4E,6E,8E)-3,7-dimethyl-9-(2,6,6-trimethyl- 1-cyclohexen-1-yl)-2,4,6,8-nonaetetraenamide); all-trans-retinylidene methyl nitrone ((Z)-α-[(E)-2,6-dimethyl- 8-(2,6,6-trimethyl-1-cyclohexen-1-yl)-1,3,5,7-octatetraenyl]-N-methylnitrone); hydroxenin ((Z)-3,7-dimethyl- 9-(2,6,6-trimethyl-1-cyclo-hexen-1-yl)nona-2,4,6-triene- 1,6-diol); Ro 12-0995 (ethyl (E)-9-(2-chloro-3,6-dimethyl- 4-methoxyphenyl)-3,7-dimethyl-2,4,6,8-nonatetraenoate); Ro 12-7554 (ethyl (E)-9-(2,6-dichloro-4-methoxy- 3-methylphenyl)-3,7-dimethyl-2,4,6,8-nonatetrenoic); Ro 10-1770 ((E)-3,7-dimethyl-9 [5,5-dimethyl- 2-(1-methoxyethyl)-1-cyclopenten-1-yl]-2,4,6,8-nonatetraenoic acid); all-trans-5, 6-epoxy-2-retinylidene-cyclohexanedione (2-[(E)-3,7-dimethyl-9-(2,2,6-trimethyl-5,6-oxacyclohex-1-yl)-2,4,6,8-nonatetraenylidene]-1,3-cyclohexanedione); Ro 21-6667

((E)-8-(4-methoxy-2,3,6-trimethylphenylthio)- 3,7-dimethyl-2,4,6-octatrienoic acid); SRI 5898-21 ((E)-6-[2-(2,6,6-trimethyl-1-cyclohexen-1-yl)ethen- 1-yl]-2-naphthalenecarboxylic acid); Ro 13-6307 ((E)-7-(5,6,7,8-tetrahydro-5,5,8,8-tetramethyl-2-naphthalenyl)- 3-methyl-2,4,6-octatrienoic acid); Ro 13-2389 (ethyl (E)-7-(5,6,7,8-tetrahydro-5,5,8,8-tetramethyl-2-naphthalenyl)- 3-methyl-2,4,6-octa-trienoate); Ro 13-4306 ((E)-3-methyl-7-(1,1,3,3-tetramethyl-5-indanyl)-2,4,6-octatrienoic acid); Ro 13-9272 ((E)-5,6,7,8-tetrahydro-2[1-(4-methylphenyl)-propen-2-yl]-5,5,8,8-tetramethylnaphthalene); Ro 13-8320 ((E)-4-[2-(5,6,7,8-tetrahydro- 5,5,8,8-tetramethyl-2-naphthalenyl)-1-propen-1-yl]phenyl-methanol); Ro 15-1570 (ethyl (E)-4-[2-(5,6,7,8-tetrahydro- 5,5,8,8 -tetramethyl-2-naphthalenyl)-1-propen-1-yl]phenyl sulfone; Ro 13-6298 (ethyl (E)-4-[2-(5,6,7,8-tetrahydro- 5,5,8,8 -tetramethyl-2-naphthalenyl)-1propen-1-yl]benzoate); Ro 15-1550 ((E)-4-[2-(1,1,3,3-tetramethylindan- 5-yl)-1-propen-1-yl]benzoic acid); SRI 6409-94 (N-(4-carbethoxyphenyl) 5,6,7,8-tetrahydro-5,5,8,8-tetramethyl- 2-naphthalenecarboxamide; SRI 7323-78 ((E)-6[2-( 4-carboxyphenyl)-1-propen-1-yl]-3,4 -dihydro-4,4-dimethyl- 2H-1-benzothiopyran); SRI 6153-40 (6-(5,6,7,8-tetrahydro- 8,8-dimethyl-2-naphthalenyl)-2 -naphthalenecarboxylic acid); SRI 5898-71 (6-(5,6,7,8-tetrahydro-5,5,8,8-tetramethyl-2-naphthalenyl)- 2-naphthalenecarboxylic acid).

M. F. Boehm et al. ((1994) "Synthesis of high specific activity [³H]-9-cis-retinoic acid and its application for identifying retinoids with unusual binding properties," *J. Med. Chem.*, Vol. 37, pp. 408–414) disclosed retinoic acid derivatives and analogs such as 9-cis-RA (9-cis-retinoic acid); TTNPB ((E)-4-[2-(5,6,7,8-tetrahydro-5,5,8,8-tetramethyl-2-naphthalenyl)-1-propenyl]benzoic acid); 3-alkyl-TTNPB((E)- 4-[2-(5,6,7,8-tetrahydro-3-alkyl-5,5,8,8-tetramethyl- 2-naphthalenyl)-1-propenyl]benzoic acid such as 3-Methyl-TTNPB ((E)-4[2-(5,6,7,8-tetrahydro-3,5,5,8,8-pentamethyl- 2-naphthalenyl)-1-propenyl]benzoic acid); 3-Ethyl-TTNPB ((E)-4[2-(5,6,7,8-tetrahydro-3-ethyl-5,5,8,8-tetramethyl- 2-naphthalenyl)-1-propenyl]benzoic acid); and 3-Isopropyl-TTNPB ((E)-4-[2-(5,6,7,8-tetrahydro-3-isopropyl- 5,5,8,8-tetramethyl-2-naphthalenyl)-1-propenyl] benzoic acid).

Other representative retinoids contemplated for use in the invention are disclosed in EP 0 11 325 B1, published Jun. 20, 1984; EP 0 263 493 A2, published Oct. 7, 1986; EP 0 274 104 A2, published Jul. 13, 1988; EP 0 303 915 B1, published Feb. 22, 1989; EP 0 100 839 B1, published Feb. 22, 1984; EP 0 263 492 A1, published Apr. 13, 1988; EP 0439 042 A1, published Jul. 31, 1991; EP 0 552 624 A1, published Jul. 28, 1993; EP 0568 898 A1, published Nov. 10, 1993; U.K. patent application GB 2 190 378 A, published Nov. 18, 1987; U.S. Pat. Nos. 4,171,318; 4,200,647; 4,231,944; 4,326,055; 4,396,553; 4,395,575; 4,544,770; 4,556,518; 4,565,863; 4,863,969; 4,870,219; 4,883,613; 4,894,480; 4,900,478; 4,935,560; 4,990,703; 5,001,276; 5,030,764; 5,030,767; 5,055,622; 5,075,333; 5,158,773; 5,242,909; and 5,252,604, which are incorporated herein by reference in their entirety.

While all-trans retinoic acid (RA) is the preferred retinoid, it will be understood that compounds which bind to retinoic acid receptors and which have anti-adhesion formation capabilities are also contemplated for use in the invention. The preferred retinoids are those compounds which have little or no toxicity, e.g., local skin irritation and systemic toxicity as hypervitaminosis A syndrome, and are suitable for topical use in animals, including humans. It is also preferred that the retinoids have little or no teratogenic or angiogenic activities.

Retinoid compounds can be ascertained by methods known in the art. One method involves the use of competitive nuclear retinoic acid (RA and RX) receptor binding assays for identifying compounds which bind directly to the receptors. For instance, J. J. Repa et al. ((1993) "All-transretinol is a ligand for the retinoic acid receptors," *Proc. Natl. Acad. Sci. USA*, Vol. 90, pp. 7293–7297) discloses a competitive RA receptor binding assay based on human neuroblastoma cell nuclear extracts. H. Törmä et al. ((1994) "Biologic activities of retinoic acid and 3,4-dehydroretinoic acid in human keratinoacytes are similar and correlate with receptor affinities and transactivation properties," *J. Invest. Dermatology*, Vol. 102, pp. 49–54) discloses assays for measuring binding affinities for the nuclear retinoic acid receptors and for measuring transcriptional activation induction. M. F. Boehm et al. ((1994) "Synthesis of high specific activity [³H]-9-cis-retinoic acid and its application for identifying retinoids with unusual binding properties," *J. Med. Chem.*, Vol. 37, pp. 408–414) discloses a ligand-binding assay and a receptor/reporter cotransfection assay for monitor regulation of gene expression. EP 0 552 612 A2, published Jul. 28, 1993, describes ligand-binding trapping assays based on incubation of radiolabeled compounds with transfected COS-1 cells which express RA and RX receptors.

While the present invention is not bound to any particular theory, it is believed that retinoids (particularly retinoic acid) may inhibit adhesion formation through a variety of mechanisms. For example, retinoids reduces the formation of tumor necrosis factor (TNF), a proinflammatory cytokine that could conceivably increase adhesion formation. K. Mehta et al. (1994). Retinoids also reduced IL-1-induced IL-6 production. IL-6 is a proinflammatory cytokine that may contribute to adhesion formation. Zitnik et al. (1994) "Retinoic Acid Inhibition of IL-1 Induced IL-6 Production by Human Lung Fibroblasts," *J. Immun.*, Vol. 152, pp. 1419–1427.

Retinoids also increase fibrinolytic enzyme activity which in turn reduces fibrin deposition which serves as a scaffold for adhesion formation. For instance, retinoids increased PMA-induced plasminogen activator production as well as the expression of urokinase receptors. W. A. Schuster et al. (1993) "Retinoic acid potentiates phorbol ester-mediated induction of urokinase and plasminogen activator inhibitor type 2 in human myeloid leukemic cell lines," *Endocrinology*, Vol. 133, pp. 1724–30; I. Immonen et al. (1993) "Retinoids increase urokinase-type plasminogen activator production by human retinal pigment epithelial cells in culture," *Invest. Ophthal.& Visual Sci.*, Vol. 34, pp. 2062–67; J. van Giezen et al. (1993) "Retinoic acid enhances fibrinolytic activity in vivo by enhancing tissue type plasminogen activator (tPA) activity and inhibits venous thrombosis," *Thrombosis and Haemostasis*, Vol. 69, pp. 381–6; R. D. Medh et al. (1992) "Stimulation of tissue plasminogen activator production by retinoic acid: synergistic effect on protein kinase C-mediated activation," *Blood*, Vol. 40, pp. 981–7. A. M. Van Bennekum et al. (1993) "Modulation of tissue type plasminogen activator by retinoids in rat plasma and tissues," *Am. J. of Physiology*, Vol. 363, R931.

Retinoids also modulate the production of thrombomodulin, tissue factor and procoagulant activity in such a way as to increase fibrinolytic activity. Increased fibrinolytic activity, as mentioned above, may inhibit adhesion formation. M. Conese et al. (1991) "Inhibitory effect of retinoids on the generation of procoagulant activity by blood mononuclear phagocytes," *Thrombosis and Haemostasis*, Vol. 66, pp.

662–5; S. Horie et al. (1993) "Retinoic acid stimulates expression of thrombomodulin, a cell surface anticoagulant glycoprotein, on human endothelial cells," *Biochem. J.*, Vol. 281, pp. 149–154; H. Ishii et al. (1992) "Retinoid acid counteracts both the downregulation of thrombomodulin and the induction of tissue factor in human endothelial cells exposed to tumor necrosis factor," *Blood*, Vol. 80, pp. 2556–62.

As is well recognized in the art, however, no one of these possible mechanisms of action of retinoic acid and other retinoids would in and of itself be sufficient to enable one to predict whether these compounds would have any utility in reduction of adhesion formation.

For instance, retinoic acid increases the production of interleukin 1 and transforming growth factor β. Both of these cytokines were shown to increase the formation of adhesions after injection into postoperative animals. Kim et al. (1992) "Effect of Topical Retinoic Acids on the Levels of Collagen mRNA During the Repair of UVB-Induced Dermal Damage in the Hairless Mouse and the Possible Role of TGF-B as a mediator," *J. Invest. Derm.*, Vol. 98, pp. 359–363; Goettsch et al. (1992) "Adjuvant Activity of all-trans-retinoic acid in C57B1/6 mice," *Int. J. Immunopharm.*, Vol. 14, pp. 143–150; A. Batova et al. "Retinoic acid induces secretion of latent transforming growth factor β1 and β2 in normal and human papillomavirus type 16-immortalized human keratinocytes (1992) *Cell Growth and Differentiation*, Vol. 3, pp. 763–72; Y. Tokura et al. (1992) "Retinoid augmentation of bioactive interleukin 1 production by murine keratinocytes," *Br. J Dermatology*, Vol. 126, pp. 485–95; A. Herschlag et al. (1991) "The effect of interleukin 1 on adhesion formation in the rat," *Am J. Obstet. Gynecol.*, Vol. 165, pp. 771–4; W. H. McBride et al. (1989) "Effect of interleukin 1, inflammation and surgery on the incidence of adhesion formation after abdominal irradiation in mice," *Cancer Res.*, Vol. 49, pp. 169–173; and R. S. Williams et al. (1992) "Effect of transforming growth factor beta on postoperative adhesion formation in intact peritoneum," *J. Surg. Res.*, Vol. 52, pp. 65–70.

Retinoids induce the production of LTC4 synthetase which may in turn increase the formation of leukotrienes, a class of proinflammatory compounds which may contribute to the formation of adhesions. Y. Hamasaki et al. (1994) "Specific induction of LTC4 synthase by retinoic acid in rat basophilic leukemia-1 cells," *Int. Arch. Allergy Immunol.*, Vol. 103, pp. 260–5.

Retinoids induce leukocyte (specifically PMN) chemotaxis and interleukin 8 production. Glasser et al., 1994; K. D. Yang et al. (1993) "Induction of interleukin 8 expression in neuroblastoma cells by retinoic acid: implication of leukocyte chemotaxis and activation," *Pediatric Res.*, Vol. 34, pp. 720–4.

Retinoids inhibit the respiratory burst of leukocytes. R. Fumarulo et al. (1991) "Retinoids inhibit the respiratory burst and degranulation of stimulated human polymorphonuclear leukocytes," *Agents and Actions*, Vol. 34, pp. 339–44. In contrast, tolmetin, a NSAID agent also shown to reduce adhesion formation, has been shown to increase the production of oxygen radicals by postoperative macrophages in rabbits (K. Rodgers et al. (1988) "Effects of tolmetin sodium dihydrate on normal and post-surgical peritoneal cell function," *Int'l. J. Immunopharm.*, Vol 10, pp. 111–120).

Retinoids induce the production of inhibitors of fibrinolysis (plasminogen activator inhibitors). As discussed under mechanism of action section above, fibrinolysis is important in the reduction of adhesion formation. Schuster et al. (1993).

Accordingly, in light of these possible mechanisms of action of retinoic acid and other retinoids, there is no suggestion that retinoids, particularly retinoic acid, would in and of itself have any utility in preventing or reducing post-surgical adhesion formation.

Pursuant to the method of the present invention, at least one retinoid is maintained in an effective concentration at the site of potential adhesion formation for a period of time sufficient to permit substantial re-epithelialization. The retinoid is typically administered over the perioperative interval, which for purposes of the present invention may include time shortly prior to surgery through the surgery itself up to some time after completion of surgery.

The term of administration may vary depending upon a number of factors which would be readily appreciated those skilled in the art. In general, administration of a retinoid in accordance with the present invention should be effected from the time of surgery for at least 24 to 48 hours after completion of the surgical procedure. In general, the retinoid may be administered from the time of surgery for a period ranging between about 24 hours and about 14 days, and preferably ranging between about 24 hours and about 7 days and most preferably ranging between about 24 and about 72 hours. As healing is in most cases complete within about two weeks, it is generally not necessary to continue administration of the retinoid in accordance with the present invention much longer than two weeks.

The concentrations of retinoid which can be administered would be limited by efficacy at the lower end and the solubility of the compound at the upper end. With respect to compositions comprising retinoid, the concentration ranges are as follows:

| General Range | Preferred Range |
| --- | --- |
| 0.1 ng–15 mg/hr | 10 ng–1 mg/hr |
| 0.04 ng–6 mg/hr/kg | 4 ng–0.4 mg/hr/kg |
| 0.007 ng–1 mg/hr/cm$^2$ | 0.67 ng–0.067 mg/hr/cm$^2$ |
| 0.0028 ng–0.4 mg/hr/cm$^2$/kg | 0.268 ng–0.027 mg/hr/cm 2/kg |

As defined herein, kg refers to body weight of the subject and cm$^2$ refers to the surface area of the injury site to be treated. The wt/hr/cm$^2$ ranges are generally used for intercavitary administration of retinoid compositions with liquid or barrier delivery systems.

The retinoid may be administered directly in a suitable vehicle, for example, a solution of 5% DMSO or 10% ethanol in saline, to a site at which it is desired to prevent adhesion formation. Pursuant to preferred embodiments of the present invention, however, at least one retinoid is administered in a single dose delivery (for example, prior to suturing after surgery) using a drug-delivery system which enables the maintenance of requisite concentrations of the compound for a period of time sufficient for re-epithelialization. A suitable drug-delivery system would itself be essentially inactive (i.e., essentially non-inflammatory and nonimmunogenic) and would permit release of the retinoid so as to maintain effective levels thereof over the desired time period.

A large variety of alternatives are known in the art as suitable for purposes of sustained release and are contemplated as within the scope of the present invention. Suitable delivery vehicles include, but are not limited to, the following: microcapsules or microspheres; liposomes and other lipid-based release systems; viscous instillates; absorbable and/or biodegradable mechanical barriers; and polymeric delivery materials, such as polyethylene oxide/polypropylene oxide block copolymers (e.g. poloxamers), poly-orthoesters, cross-linked polyvinyl alcohol, polyanhydrides, polymethacrylate and polymethacryladmide hydrogels, anionic carbohydrate polymers, etc. Useful delivery systems are well known in the art and are described in, e.g., U.S. Pat. No. 4,937,254, the entire disclosure of which is hereby incorporated by reference.

One particularly suitable formulation to achieve the desired near zero-order release of retinoids comprise injectable microcapsules or microspheres prepared from a biodegradable polymer, such as poly(dl-lactide), poly(dl-lactide-co-glycolide), poly-caprolactone, polyglycolide, polylactic acid-co-glycolide, poly(hydroxybutyric acid), a polyorthoester or a polyacetal. Encapsulation of retinoic acid in microspheres of biodegradable polymers has already been reported. For instance, poly(DL-lactide-co-glycolide) were found to be useful in sustained release of the drug in rabbit models of proliferative vitreoretinopathy. G. G. Giordano et al. (1993) "Sustained Delivery of Retinoic Acid from Microspheres of Biodegradable Polymer in PVR," *Investig. Ophthal. Vis. Sci.*, Vol. 34, pp. 2743–2751.

Injectable systems comprising microcapsules or microspheres of a diameter on the order of about 50 to about 500 μm offer advantages over other delivery systems. For example, they generally use less active agent and may be administered by paramedical personnel. Moreover, such systems are inherently flexible in the design of the duration and rate of separate drug release by selection of microcapsule size, drug loading and dosage administered. In addition, such microcapsules can be successfully sterilized with gamma irradiation.

Microcapsules are systems comprising a polymeric wall that encloses a liquid or solid core. The capsule wall usually does not react with the core material; however, it is designed to provide sufficient strength to enable normal handling without rupture while being sufficiently thin to allow a high core to wall volume ratio. The capsule contents remain within the wall until released by diffusion or other means that dissolve, melt, break, rupture or remove the capsule material. Preferably, the capsule wall can be made to degrade and decompose in suitable environments while diffusing the core material through the capsule wall to allow for its slow, prolonged delivery.

The mechanism of release in biodegradable microcapsules is a combination of drug diffusion and polymer biodegradation. Therefore, the rate and duration of release are determined by microcapsule size, drug content and quality, and polymer parameters such as crystallinity, molecular weight and composition. In particular, adjustment in the amount of drug released is generally achieved by modification of capsule wall thickness, capsule diameter, or both. Detailed information concerning the design, preparation and use of microspheres and microcapsules is provided by, e.g., Lewis, D. H., "Controlled Release of Bioactive Agents from Lactide/Glycolide Polymers," in "Biodegradable Polymers as Drug Delivery Systems," Jason & Langer, eds., pp. 1–41 (1990), the entire disclosure of which is hereby incorporated by reference. The sustained intraperitoneal release of dexamethasone using poly(lactide-co-glycolide) microparticles is described in Hoeckel, M. et al., "Prevention of Peritoneal Adhesions in the Rat with Sustained Intraperitoneal Dexamethasone Delivered by a Novel Therapeutic System," *Annales Chirurgiae et Gynaecologiae*, Vol. 76, pp. 306–313 (1987), the entire disclosure of which is also incorporated by reference.

As is well known to those skilled in the art, various methods are currently available for preparing microcapsules, any of which could be employed to provide formulations in accordance with the present invention. Biodegradable polymeric materials suitable for preparation of microcapsules for controlled (i.e., near zero-order) release would be readily determined through routine experimentation by those skilled in the art. Moreover, alternative delivery systems suitable for use in accordance with the present invention (for example, fibers or filaments comprising the active agents) based on biodegradable polymers are also contemplated as within the scope of the present invention.

An alternative approach for the single-dose delivery of at least one retinoid involves the use of biodegradable polymers, such as the ones described above, in the form of a film. Such films may be produced by spraying or discharging dispersed liquid droplets containing the biopolymer and the retinoid in a suitable carrier from a pressurized container onto the targeted site.

Another approach for the single-dose delivery of at least one retinoid, in accordance with the present invention, involves the use of liposomes and other lipid-based delivery systems. The encapsulation of an active agent in multilamellar vesicles (or liposomes) is a well known technique used to assist in target drug delivery and prolong drug residence. In a typical procedure, a liposome-forming powdered lipid mixture is added to the desired quantity of active agent in aqueous solution (e.g., phosphate buffered saline) to form a suspension. After a suitable hydration period, the hydrated suspension is then autoclaved to provide the liposome-active agent preparations. A lipid mixture suitable for formation of liposomes may be prepared from L-alpha-distearoyl phosphatidylcholine and cholesterol dissolved in chloroform, to which alpha-tocopherol is added; other compositions and methods for formation of liposomes would, however, also be useful for this purpose. The intraperitoneal administration of liposomes containing ibuprofen or tolmetin is described in Rodgers, K. et al., "Inhibition of Postsurgical Adhesions by Liposomes Containing Nonsteroidal Anti-inflammatory Drugs," *Int. J. Fertil.*, Vol. 35, p. 40 (1990), the entire disclosure of which is hereby incorporated by reference.

Other lipid-based delivery systems are also contemplated for use in this invention. One useful system includes lipid foams such as DepoFoam extended-release formulations comprising spherical particles bounded by a single bilayer lipid membrane and each containing numerous nonconcentric aqueous chambers which encapsulate the active ingredient (see, e.g, Kim, T. K. et al. (1993) "Extended-release formulation of morphine for subcutaneous administration," *Cancer Chemother. Pharmacol.*, Vol. 33, 187; Chatelut, E. et al. (1993) "A slow-release methotrexate formulation for intrathecal chemotherapy," *Cancer Chemother. Pharmacol.*, Vol. 32, 179.] Such lipid particles are made from nontoxic lipids identical to those found in cell membranes.

Another lipid-based delivery system for delivering the retinoids according to the invention includes emulsion carrier systems based on egg sphinomyelin and egg phosphatidylcholine. Such emulsion carrier systems have prolonged blood circulation retention times and were developed for delivering highly lipophilic drugs such as retinoic acid. T. Takino et al. (1994) "Long Circulating Emulsion Carrier Systems for Highly Lipophilic Drugs," *Biol. Pharm. Bull.*, Vol. 17, pp. 121–125.

Yet another suitable approach for single dose delivery of at least one retinoid in accordance with the present invention involves the use of so-called viscous instillates. In this technique, high-molecular-weight carriers used in admixture with the active agents include, but are not limited to, the following: dextrans and cyclodextrans; hydrogels; cross-linked viscous materials, including viscoelastics and cross-linked viscoelastics; carboxymethylcellulose; and hyaluronic acid. While some studies have suggested that the use of viscous barrier solutions per se may have an advantageous effect in reducing the incidence of adhesion formation, it is believed that any such effect is of limited scope when compared to the combination of at least one retinoid and carrier. The intraperitoneal administration of a viscous instillate comprising tolmetin is described in Abe, H. et al., "The Effect of intra-peritoneal Administration of Sodium Tolmetin-Hyaluronic Acid on the Postsurgical Cell Infiltration In Vivo," *J Surg. Res.*, Vol 49, p. 322 (1990), the entire disclosure of which is hereby incorporated by reference.

Pursuant to yet another approach, at least one retinoid is administered in combination with an absorbable mechanical barrier which alone reduces adhesion formation. As would be readily apparent to one working in the field, at least one retinoid may be covalently or non-covalently (e.g., ionically) bound to such a barrier, or it may simply be dispersed therein. A particularly suitable mechanical barrier for use in this particular embodiment of the invention comprises oxidized regenerated cellulose; one such absorbable barrier is available under the designation INTERCEED(TC7) from Johnson and Johnson Medical, Inc., New Brunswick, N.J. [INTERCEED(TC7) Adhesion Barrier Study Group, "Prevention of postsurgical adhesions by INTERCEED(TC7), an absorbable adhesion barrier: a prospective, randomized multicenter clinical study," *Fertility and Sterility*, Vol. 51, p. 933 (1989)]. The use of a mechanical barrier as a carrier to deliver heparin to traumatized surfaces is disclosed in Diamond, M. P. et al., "Synergistic effects of INTERCEED(TC7) and heparin in reducing adhesion formation in the rabbit uterine horn model," *Fertility and Sterility*, Vol. 55, p. 389 (1991) and Diamond, M. P. et al., "Adhesion reformation: reduction by the use of INTERCEED(TC7) plus heparin," *J. Gyn. Surg.*, Vol. 7, p. 1 (1991), the entire disclosures of which are hereby incorporated by reference.

The invention may be better understood with reference to the accompanying examples, which are intended to be illustrative only and should not be viewed as in any sense limiting the scope of the invention, which is defined hereinafter in the accompanying claims.

EXAMPLES

Multiple studies to confirm the efficacy of retinoic acid in the reduction of adhesion formation after peritoneal surgery were performed. Two model systems were employed: the sidewall adhesion model and the uterine horn model. A clear correlation between results obtained using both of these models and utility in adhesion prevention has been demonstrated with INTERCEED(TC7), for which clear clinical efficacy has been shown and FDA approval for adhesion prevention in gynecological surgery has been obtained.

In the peritoneal sidewall model, rabbits were pre-anesthetized with 1.2 mg/kg acetylpromazine and anesthetized with a mixture of 55 mg/kg ketamine hydrochloride and 5 mg/kg xylazine intramuscularly. Following preparation for sterile surgery, a midline laparotomy was performed. A 3×5-cm area of peritoneum and transversus abdominis muscle was removed on the right lateral abdominal wall. The cecum was exteriorized, and digital pressure was exerted to create subserosal hemorrhages over all cecal surfaces. The cecum was then returned to its normal anatomic position. The compound to be tested was placed in an Alzet minoosmotic pump (Alza Corporation, Palo Alto, Calif., USA) to allow continuous release of the molecule through the postsurgical interval. The Alzet miniosmotic pump was placed in the subcutaneous space and a delivery tube connected the pump with the site of injury at sidewall. Vehicle was placed in the pump of control rabbits. The abdominal wall and skin were closed in a standardized manner.

After 7 days, the rabbits were sacrificed and the percentage of the area of the sidewall injury that is involved in adhesions was determined. In addition, the tenacity of the adhesion formed was scored use a system as follows:

0=NO adhesions

1=mild, easily dissectable adhesions

2=moderate adhesions; non-dissectable, does not tear organ

3=dense adhesions; non-dissectable, tears when removed

A reduction in the area or the tenacity of the adhesions would be considered beneficial.

In additional experiments, a rabbit uterine horn model was employed. This model has been previously shown to cause severe adhesions in rabbits after surgery [Nishimura, K. et al., "The Use of Ibuprofen for the Prevention of Postoperative Adhesions in Rabbits," *Am. J. Med.*, Vol. 77, pp. 102–106 (1984)]. The rabbits were anesthetized (130 mg/kg ketamine and 20 mg/kg acetylpromazine im) and prepared for sterile surgery. A midline laparotomy was performed, and surgical trauma was performed on both uterine horns by abrading the serosal surface with gauze until punctate bleeding developed. Ischemia of both uterine horns was induced by removal of the collateral blood supply. After traumatization, the abdominal wall was closed in two layers. The compound to be tested was delivered as described for the peritoneal sidewall model, but the tubing was placed over the injured uterine horns.

With the uterine horn model, an initial score to represent the overall extent of adhesions is given (0 to 4+). The percentage of a surface of the horn involved in adhesions to various organs are given in the tables below the overall adhesion score.

In the model systems employed in the examples reported herein, the exemplary compound retinoic acid (RA) was shown to reduce the incidence of peritoneal adhesions. In these Examples, the drug was delivered at a rate of 10 µl/hour. The concentration ranges employed were 0.01 to 0.1 mg/ml. For purposes of preventing adhesion formation in accordance with the present invention, it is not believed that high systemic levels of retinoic acid would be necessary.

Example 1

The efficacy of retinoic acid in preventing adhesion formation was evaluated in the sidewall model. The drug was delivered for 7 days at a rate of 10 µl/hr and the animals were sacrificed after 7 days. The vehicle was 10% ethanol in saline. Relative to the control, retinoic acid was found to be efficacious in adhesion reduction in the rabbit sidewall model. The results are summarized in Table 1. A student t test analysis of the data was performed and the results are reported in Table 1 as well.

TABLE 1

| TREATMENT | % ADHESIONS | ADHESION SCORE |
|---|---|---|
| Vehicle Control | 100% | 3+ |
| | 100% | 2+ |
| | 80% | 3+ |
| | 100% | 3+ |
| | 70% | 2+ |
| | 70% | 3+ |
| Mean: | 86.7% ± 13.7 | |
| 0.1 mg/ml Retinoic acid | 0% | 0+ |
| | 0% | 0+ |
| | 50% | 2+ |
| | 40% | 2+ |
| | 0% | 0+ |
| | 20% | 1+ |
| Mean[a]: | 16.3% ± 20.3 | |
| 0.01 mg/ml Retinoid Acid | 10% | 1+ |
| | 40% | 2+ |
| | 0% | 0+ |
| | 0% | 0+ |
| | 90% | 3+ |
| | 10% | 2+ |
| Mean[b]: | 25.0% ± 32.0 | |

[a]: $p = 0.000$
[b]: $p = 0.001$

Example 2

Retinoic acid was examined in the double uterine horn model for adhesion prevention. The drug was delivered for 7 days at a rate of 10 μl/hour and the animals were sacrificed at day 7. The statistical analysis done on the data from the double uterine horn model (nonparametric data) is done on the overall score. The data is rank ordered, a rank value given and an analysis of variance on the ranks is performed. The results are summarized in Tables 2 and 3. Retinoic acid (especially at the low dose) was efficacious at the reduction of adhesions in the rabbit double uterine horn model.

TABLE 2

| TREATMENT | OVERALL ADHESION SCORE |
|---|---|
| Vehicle Control | 3+ |
| | 4+ |
| | 3+ |
| | 3+ |
| | 3.5+ |
| | 3+ |
| 0.1 mg/ml Retinoic acid | 1.5+ |
| | 0.5+ |
| | 2+ |
| | 1.5+ |
| | 2+ |
| | 1.5+ |
| 0.01 mg/ml Retinoic acid | 1+ |
| | 1.5+ |
| | 1+ |
| | 1+ |
| | 1.5+ |
| | 1+ |

TABLE 3

| | % Organ Involvement in Uterine Horn Adhesion | | | | | | | |
|---|---|---|---|---|---|---|---|---|
| | Right Horn | | | | Left Horn | | | |
| Treatment | Bowel | Bladder | Itself | Left | Bowel | Bladder | Itself | Right |
| Control | 50 | 100 | 0 | 30 | 50 | 100 | 0 | 30** |
| | 60 | 20 | 30 | 40 | 60 | 20 | 70 | 40** |
| | 40 | 20 | 30 | 50 | 40 | 20 | 30 | 50** |
| | 30 | 20 | 20 | 50 | 30 | 20 | 20 | 50** |
| | 40 | 10 | 80 | 100 | 40 | 10 | 80 | 100 |
| | 60 | 30 | 50 | 50 | 60 | 30 | 50 | 50** |
| Mean | 46.7 | 33.3 | 35 | 53.3 | 46.7 | 33.3 | 41.7 | 53.3 |
| 0.1 mg/ml Retinoid Acid | 10 | 0 | 40 | 0 | 10 | 0 | 50 | 0 |
| | 0 | 0 | 0 | 0 | 0 | 0 | 50 | 0 |
| | 10 | 20 | 20 | 0 | 20 | 20 | 40 | 0 |
| | 0 | 0 | 30 | 10 | 0 | 0 | 20 | 10 |
| | 30 | 0 | 30 | 40 | 30 | 0 | 30 | 40 |
| | 40 | 0 | 10 | 40 | 40 | 0 | 10 | 40* |
| Mean | 16.7 | 3.3 | 21.7 | 15 | 16.7 | 3.3 | 33.3 | 15 |
| 0.01 mg/ml Retinoic Acid | 0 | 10 | 0 | 0 | 0 | 10 | 30 | 0* |
| | 10 | 0 | 0 | 30 | 10 | 0 | 10 | 30 |
| | 0 | 10 | 30 | 0 | 0 | 10 | 0 | 0 |
| | 0 | 20 | 10 | 0 | 0 | 20 | 0 | 0 |
| | 10 | 0 | 10 | 0 | 10 | 0 | 40 | 0 |
| | 0 | 0 | 30 | 30 | 0 | 0 | 30 | 30* |
| Mean | 3.3 | 6.7 | 13.3 | 10 | 3.3 | 6.7 | 18.3 | 10 |

*Bladder and/or bowel adhered to sidewall at the tube or suture for the tube.
**Horn along with bowel and/or bladder adhered to sidewall at the tube or the suture for the tube.

Statistical analysis was performed on the overall score of the nonparametric data taken from Table 2. The data was rank ordered and assigned a rank value. Analysis of the variance of the ranks was then performed and the resulting student t test results are summarized below.

| Treatment | Rank order | p value |
|---|---|---|
| Control | 15.5 ± 1.4 | — |
| 0.1 mg/ml Retinoic acid | 8.0 ± 3.5 | 0.000 |
| 0.01 mg/ml Retinoic acid | 5.0 ± 2.1 | 0.000 |

Example 3

The efficacy of retinoic acid in the double uterine horn model was further evaluated in a kinetics study. In this study, the pump was disconnected at various times after surgery to determine the time period of exposure to the drug effective to reduce adhesion formation. The efficacy of retinoids in preventing adhesions improved at longer exposure times (72 hours) for the two concentrations tested. The results are summarized in Tables 4 and 5.

TABLE 4

| TREATMENT | OVERALL ADHESION SCORE |
|---|---|
| Vehicle Control | 3+ |
| | 3+ |
| | 3.5+ |
| | 3+ |
| | 3+ |
| | 3+ |
| 0.1 mg/ml RA 24 hour D/C | 1.5+ |
| | 1+ |
| | 1.5+ |

TABLE 4-continued

| TREATMENT | OVERALL ADHESION SCORE |
|---|---|
| | 1.5+ |
| | 2+ |
| | 1.5+ |
| 0.1 mg/ml PA 48 hour D/C | 2.5+ |
| | 1.5+ |
| | 1.5+ |
| | Died |
| | 1.5+ |
| | 1+ |
| 0.1 mg/ml RA 72 hour D/C | 2+ |
| | 2.5+ |
| | 0.5+ |
| | 1.5+ |
| | 1+ |
| 0.01 mg/ml RA 24 hour D/C | 1.5+ |
| | 1.5+ |
| | 2.5+ |
| | 1+ |
| | 2+ |
| | 2+ |
| 0.01 mg/ml RA 48 hour D/C | 1.5+ |
| | 1+ |
| | 1.5+ |
| | 2+ |
| | 1+ |
| | 1.5+ |
| 0.01 mg/ml RA 72 hour D/C | 1.5+ |
| | 1.5+ |
| | 1+ |
| | 2+ |
| | 1+ |
| | 1.5+ |

TABLE 5

| | % Organ Involvement in Uterine Horn Adhesion | | | | | | | |
|---|---|---|---|---|---|---|---|---|
| | Right Horn | | | | Left Horn | | | |
| Treatment | Bowel | Bladder | Itself | Left | Bowel | Bladder | Itself | Right |
| Control | 30 | 40 | 40 | 30 | 30 | 40 | 20 | 30** |
| | 30 | 60 | 40 | 20 | 30 | 60 | 30 | 20 |
| | 30 | 80 | 60 | 60 | 30 | 80 | 60 | 60* |
| | 20 | 50 | 20 | 40 | 30 | 50 | 20 | 40** |
| | 50 | 10 | 40 | 40 | so | 10 | 0 | 40 |
| | 30 | 70 | 30 | 40 | 30 | 70 | 40 | 40* |
| Mean | 33.3 | 51.7 | 38.3 | 38.3 | 33.3 | 51.7 | 28.3 | 38.3 |
| 0.1 mg/ml RA 24 D/C | 10 | 0 | 30 | 10 | 10 | 0 | 20 | 10 |
| | 10 | 0 | 20 | 0 | 10 | 0 | 10 | 0 |
| | 0 | 0 | 20 | 10 | 0 | 0 | 20 | 10 |
| | 20 | 10 | 10 | 0 | 20 | 10 | 0 | 0 |
| | 30 | 0 | 10 | 10 | 30 | 0 | 10 | 10** |
| | 0 | 10 | 20 | 10 | 0 | 10 | 10 | 10 |
| Mean | 11.7 | 3.3 | 18.3 | 6.7 | 11.7 | 3.3 | 11.7 | 6.7 |
| 0.1 mg/ml RA 48 D/C | 10 | 30 | 10 | 10 | 10 | 30 | 10 | 10 |
| | 0 | 30 | 10 | 10 | 0 | 30 | 0 | 10* |
| | 0 | 50 | 30 | 0 | 0 | 50 | 0 | 0 |
| | | | | DIED D6 P/O | | | | |
| | 10 | 10 | 10 | 0 | 10 | 10 | 10 | 0 |
| | 20 | 0 | 20 | 0 | 20 | 0 | 0 | 0** |
| Mean | 8 | 24 | 16 | 4 | 8 | 24 | 4 | 4 |
| 0.1 mg/ml RA | 0 | 30 | to | 10 | 0 | 30 | 10 | 10 |

TABLE 5-continued

| | % Organ Involvement in Uterine Horn Adhesion | | | | | | | |
|---|---|---|---|---|---|---|---|---|
| | Right Horn | | | | Left Horn | | | |
| Treatment | Bowel | Bladder | Itself | Left | Bowel | Bladder | Itself | Right |
| 72 D/C | | | | | | | | |
| | 10 | 20 | 20 | 20 | 10 | 20 | 20 | 20 |
| | 0 | 0 | 20 | 0 | 0 | 0 | 20 | 0 |
| | 0 | 20 | 10 | 10 | 0 | 20 | 10 | 10 |
| | 20 | 0 | 20 | 10 | 20 | 0 | 0 | 10 |
| | 0 | 0 | 30 | 10 | 0 | 0 | 10 | 10 |
| Mean | 5 | 11.7 | 18.3 | 10 | 5 | 11.7 | 11.7 | 10 |
| 0.01 mg/ml RA 24 D/C | 10 | 0 | 20 | 20 | 10 | 0 | 20 | 20 |
| | 10 | 0 | 10 | 10 | 10 | 0 | 10 | 10 |
| | 20 | 10 | 30 | 20 | 20 | 10 | 0 | 20 |
| | 0 | 10 | 10 | 0 | 0 | 10 | 0 | 0 |
| | 40 | 10 | 0 | 0 | 40 | 10 | 20 | 0** |
| | 30 | 0 | 20 | 20 | 30 | 0 | 20 | 20** |
| Mean | 18.3 | 5 | 15 | 11.7 | 18.3 | 5 | 11.7 | 11.7 |
| 0.01 mg/ml RA 48 D/C | 0 | 30 | 30 | 0 | 0 | 30 | 0 | 0 |
| | 0 | 10 | 10 | 0 | 0 | 10 | 20 | 0 |
| | 20 | 0 | 60 | 10 | 0 | 0 | 60 | 10 |
| | 30 | 20 | 20 | 0 | 30 | 20 | 20 | 0 |
| | 0 | 0 | 30 | 0 | 0 | 0 | 20 | 0 |
| | 20 | 0 | 0 | 10 | 20 | 0 | 20 | 10 |
| Mean | 11.7 | 10 | 25 | 3.3 | 8.3 | 10 | 23.3 | 3.3 |
| 0.01 mg/ml RA 72 D/C | 0 | 20 | 20 | 0 | 0 | 20 | 30 | 0 |
| | 0 | 0 | 30 | 10 | 0 | 0 | 20 | 10 |
| | 0 | 0 | 30 | 10 | 0 | 0 | 20 | 10 |
| | 10 | 30 | 20 | 0 | 10 | 30 | 10 | 0 |
| | 0 | 20 | 10 | 0 | 0 | 0 | 10 | 0 |
| | 10 | 10 | 20 | 0 | 10 | 10 | 0 | 0* |
| Mean | 3.3 | 13.3 | 21.7 | 3.3 | 3.3 | 10 | 15 | 3.3 |

Statistical analysis was performed on the overall score of the nonparametric data taken from Table 4. The data was rank ordered and assigned a rank value. Analysis of the variance of the ranks was then performed and the resulting student t test results are summarized below.

| Test System | Time | Rank Score | p value |
|---|---|---|---|
| Control | — | 38.5 ± 1.1 | — |
| 0.1 mg/ml Retinoic acid | 24 | 16.1 ± 7.9 | 0.000 |
| | 48 | 18.7 ± 9.1 | 0.000 |
| | 72 | 14.2 ± 12.7 | 0.000 |
| 0.01 mg/ml Retinoic acid | 24 | 22.4 ± 9.7 | 0.002 |
| | 48 | 15.8 ± 8.3 | 0.000 |
| | 72 | 15.8 ± 8.3 | 0.000 |

While the fundamental novel features of the invention has been shown and described, it will be understood that various omissions, substitutions and changes in the form and details illustrated may be made by those skilled in the art without departing from the spirit of the invention. It is the intention, therefore, to be limited only as indicated by the scope of the following claims.

What is claimed is:

1. A method for preventing post-surgical adhesion formation between organ surfaces, comprising administering an effective amount of at least one retinoid to a site of surgical activity on an organ surface for a period of time sufficient to permit tissue repair.

2. A method according to claim 1 wherein said retinoid comprises retinoic acid.

3. A method according to claim 1, wherein said tissue repair comprises re-epithelization.

4. A method according to claim 1, wherein said tissue repair comprises mesothelial repair.

5. A method according to claim 1, wherein the retinoid is administered in conjunction with a delivery vehicle which maintains an effective local concentration of said retinoid compound at said site.

6. A method according to claim 5, wherein said effective local concentration ranges between about 0.007 ng and about 1 mg/hr/cm$^2$.

7. A method according to claim 6, wherein said effective local concentration ranges between about 0.67 ng and about 0.067 mg/hr/cm$^2$.

8. A method according to claim 5, wherein said effective local concentration ranges between about 0.04 ng and about 6 mg/hr/kg.

9. A method according to claim 8, wherein said effective local concentration ranges between about 4 ng and about 0.4 mg/hr/kg.

10. A method according to claim 5, wherein the delivery vehicle comprises microcapsules or microspheres.

11. A method according to claim 10, wherein the microcapsules or microspheres comprise a biodegradable polymer selected from the group consisting of poly(dl-actides), poly(dl-lactide-co-glycolides), polycaprolactones, polyglycolides, polylactic acid-co-glycolides, poly(hydroxybutyric acids), polyortho-esters, polyacetals and mixtures thereof.

12. A method according to claim 5, wherein the delivery vehicle is a film.

13. A method according to claim 12, wherein the film comprises a biodegradable polymer selected from the group consisting of poly(dl-lactides), poly(dl-lactide-co-glycolides), polycaprolactones, polyglycolides, polylactic acid-co-glycolides, poly(hydroxybutyric acids), polyorthoesters, polyacetals and mixtures thereof.

14. A method according to claim 5, wherein the delivery vehicle comprises liposomes.

15. A method according to claim 14, wherein the liposomes comprise L-alpha-distearoyl phosphatidylcholine.

16. A method according to claim 5, wherein the delivery vehicle comprises a lipid foam.

17. A method according to claim 5, wherein the delivery vehicle is an instillate.

18. A method according to claim 17, wherein the instillate comprises a high-molecular-weight carrier selected from the group consisting of dextrans, cyclodextrans, hydrogels, carboxymethylcellulose, hyaluronic acid, chondroitin sulfate and mixtures thereof.

19. A method according to claim 5, wherein the delivery vehicle is an absorbable mechanical barrier.

20. A method according to claim 19, wherein the absorbable mechanical barrier comprises oxidized regenerated cellulose.

* * * * *